United States Patent [19]
Born et al.

[11] Patent Number: 5,679,626
[45] Date of Patent: Oct. 21, 1997

[54] ETHYLENIC HYDROCARBONS SULPHURIZED BY ELEMENTAL SULPHUR IN THE PRESENCE OF ALKALI OR ALKALINE-EARTH METAL HYDROXICES AND IN THE PRESENCE OF GLYCOLS OR POLYGLCOLS, OR THEIR ALKYL ETHERS, AND OR WATER

[75] Inventors: Maurice Born, Nanterre; Bruno Delport, Paris; Thierry Lacome, Rueil Malmaison, all of France

[73] Assignee: Institut Francais du Petrole, Rueil Malmaison, France

[21] Appl. No.: 563,794

[22] Filed: Nov. 28, 1995

[30] Foreign Application Priority Data

Nov. 28, 1994 [FR] France ................... 94 14210
Nov. 28, 1994 [FR] France ................... 94 14208

[51] Int. Cl.⁶ .................................. C10M 135/04
[52] U.S. Cl. .................. 508/342; 508/322; 568/18; 568/21
[58] Field of Search ................... 252/45; 568/18, 568/21; 508/342, 322

[56] References Cited

U.S. PATENT DOCUMENTS

| | | | |
|---|---|---|---|
| 3,673,090 | 6/1972 | Waldbillig et al. | 252/45 |
| 3,882,031 | 5/1975 | Askew et al. | 252/45 |
| 4,097,474 | 6/1978 | Askew et al. | 260/139 |
| 4,119,549 | 10/1978 | Davis | 252/45 |
| 4,225,488 | 9/1980 | Horodysky et al. | 252/45 |
| 4,284,520 | 8/1981 | Bolle et al. | 568/21 |
| 4,584,113 | 4/1986 | Walsh | 252/45 |
| 4,739,036 | 4/1988 | Colvin et al. | 528/389 |
| 4,983,558 | 1/1991 | Born et al. | 502/31 |
| 5,133,889 | 7/1992 | Born et al. | 568/26 |
| 5,135,670 | 8/1992 | Johnson et al. | 252/45 |
| 5,232,623 | 8/1993 | Shaw | 252/183.18 |
| 5,286,395 | 2/1994 | Born et al. | 252/45 |
| 5,338,468 | 8/1994 | Arvizzigno et al. | 252/45 |
| 5,403,960 | 4/1995 | Kadkhodayan et al. | 568/21 |
| 5,410,088 | 4/1995 | Harris et al. | 568/21 |

FOREIGN PATENT DOCUMENTS

| | | |
|---|---|---|
| 0 201 197 | 11/1986 | European Pat. Off. . |
| 0 258 168 | 3/1988 | European Pat. Off. . |
| 734249 | 5/1980 | U.S.S.R. ........ C10M 135/04 |
| 748 694 | 6/1953 | United Kingdom . |
| 1 067 378 | 5/1967 | United Kingdom . |
| 1 404 714 | 9/1975 | United Kingdom . |

OTHER PUBLICATIONS

Chemical Abstract, vol. 100(18), Abstract No. 142011m, 20 Apr. 1984.

*Primary Examiner*—Ellen M. McAvoy
*Attorney, Agent, or Firm*—Millen, White, Zelano, & Branigan, P.C.

[57] ABSTRACT

Sulphur-containing substances are derived from mono- or polyethylenic hydrocarbons by sulphurization using elemental sulphur in the presence of at least one alkali or alkaline-earth metal hydroxide and at least one glycol or polyglycol, or glycol or polyglycol monoether and/or water. Sulphur-containing substances, which may contain 20% to 70% by weight of sulphur, are generally soluble in lubricants to improve antiwear and extreme pressure properties. They can also be used as sulphurization agents, in particular for preparing catalysts for refining petroleum products.

11 Claims, No Drawings

ETHYLENIC HYDROCARBONS SULPHURIZED BY ELEMENTAL SULPHUR IN THE PRESENCE OF ALKALI OR ALKALINE-EARTH METAL HYDROXICES AND IN THE PRESENCE OF GLYCOLS OR POLYGLCOLS, OR THEIR ALKYL ETHERS, AND OR WATER

The invention concerns novel sulphur-containing substances, a process for their preparation and their use.

Various sulphur-containing organic substances have long been used as additives for lubricants, in particular to improve antiwear and extreme pressure properties. In particular, they are used in lubricants for highly loaded gears or metal working lubricants.

Sulphur-containing organic substances for use as antiwear and extreme pressure additives have been widely described and are obtained by various processes, which principally comprise the following two steps:

1) forming an addition product between a sulphur chloride (sulphur mono- or dichloride) and a compound containing an ethylenic unsaturation; and 2) reacting this addition product with a sulphur-containing product: a sulphide, hydrosulphide or polysulphide of an alkali metal (for example sodium) used as is or formed in situ by reacting hydrogen sulphide ($H_2S$) or mercaptans with an alkali metal hydroxide (for example sodium hydroxide). In order to increase the sulphur content in the substances obtained, elemental sulphur can be used during the second step described above.

Because chlorine-containing compounds are used in the first step of the preparation, sulphur-containing substances of this type always contain a certain residual amount of chlorine. Various improvements to the process, in particular our own, have been able to reduce this to less than 250 ppm. In addition, these processes cause formation of alkali metal chlorides (generally NaCl) and hydrosoluble organic alkaline derivatives as by-products, which are recovered as a highly polluting aqueous solution in large quantities which is thus very expensive to eliminate.

A number of processes for the preparation of sulphur-containing substances which do not use chlorine-containing compounds is known. Some of these processes involve the sulphurization of olefins by elemental sulphur and hydrogen sulphide ($H_2S$); these processes have the drawback of using a highly toxic reactant which is difficult to store and transport, and the processes develop very high pressures which can reach 90 bars, for example.

Other processes use elemental sulphur and alkaline or alkaline-earth hydrosulphides.

We have now discovered that it is possible to prepare sulphur-containing substances from mono- or polyethylenic hydrocarbons using elemental sulphur as the sole sulphur-containing reactant by operating in the presence of at least one alkali or alkaline-earth metal hydroxide and in the presence of at least one glycol or polyglycol, or glycol or polyglycol monoether, and/or water.

The sulphur-containing substances of the invention are free of chlorine, and generally have a sulphur content of about 20% to 70% by weight, depending on the starting ethylenic hydrocarbon.

The sulphur-containing substances of the invention are soluble to different degrees in mineral oils and in hydrogenated polyalphaolefins, even—and this is completely unexpected—substances with a high sulphur content.

The sulphur-containing substances of the invention can generally be defined by the fact that they are obtained by reacting at least one mono- or polyethylenic hydrocarbon which generally contains 2 to 36 carbon atoms and 1 to 3 ethylenic unsaturations with a suitable quantity of elemental sulphur in the presence of an alkali or alkaline-earth metal hydroxide and at least one alkyleneglycol or polyalkyleneglycol with a molecular weight of up to about 200, or a monoether derivative thereof, and/or water.

The starting mono- or polyethylenic hydrocarbons may be open chain, linear or branched, or cyclic. Examples are ethylene, propylene, 1-butene, n-2-butenes, isobutene, the pentenes, the hexenes (for example 2,3-dimethyl 1-butene), 1,3-butadiene, isoprene, cyclopentadiene, dicyclopentadiene, dimers and trimers of isobutene, trimers and tetramers of propylene, and non hydrogenated polyalphaolefins with low molecular weights (for example, up to about 500). Isobutene is preferably used.

The alkali or alkaline-earth metal hydroxide can be selected from sodium hydroxide, potassium hydroxide, lithium hydroxide and calcium hydroxides (lime) or barium hydroxide (barite). Sodium or potassium hydroxide is normally used.

The proportion of alkali or alkaline-earth metal hydroxide used is an amount of $3 \times 10^{-3}$ to 1.2 per ethylenic unsaturation of the starting hydrocarbon.

Surprisingly, the alkali or alkaline-earth metal hydroxide can be used in very small amounts (quasi catalytic) and the final sulphur-containing products do not contain alkali or alkaline-earth metals and exhibit no basic properties. It can be considered that the hydroxide essentially acts as a catalyst promoter for the sulphurization reaction.

When the alkali or alkaline-earth metal hydroxide is used in the presence of water, the proportion of water can be, for example, 50 to 500 $cm^3$ per ethylenic unsaturation of the starting hydrocarbon. In this case, the proportion of elemental sulphur used is up to about 250 g (i.e., about 8 moles) per ethylenic unsaturation of the starting hydrocarbon.

Still within the scope of the invention, at least one glycol, polyglycol and/or glycol or polyglycol alkyl monoether derivative can be used. In this case, the proportion of alkali or alkaline-earth metal hydroxide used is generally 0.004 to 1 mole per ethylenic unsaturation of the starting hydrocarbon.

Examples of glycols and polyglycols and their monoether derivatives which can be used with the alkali or alkaline-earth metal hydroxide are ethyleneglycol, propyleneglycol, di-, tri- and tetraethyleneglycols, di-, tri- and tetrapropyleneglycols and their alkyl monoether derivatives where the alkyl group contains 1 to 30 carbon atoms. These compounds can be used alone or as mixtures. Preferably, ethyleneglycol, propyleneglycol and their monomethylethers are used.

The proportion of glycol or glycol derivative can vary widely. In particular, it can be about 10 to 150 g per starting mono- or polyethylenic unsaturation. In this case, a proportion of elemental sulphur of up to 200 g (i.e., about 6 moles) per ethylenic unsaturation of the starting hydrocarbon can be used.

The proportion of water when present in the reaction medium with the glycol, polyglycol or monoalkyl ether can be up to, for example, 20 g per ethylenic unsaturation of the starting hydrocarbon.

The reaction is generally carried out at a temperature of 50° C. to 200° C., usually 90° C. to 160° C.

The pressure, which primarily depends on the nature of the starting mono- or polyethylenic hydrocarbons, can be from atmospheric pressure up to 50 bars, for example. Thus, for gaseous ethylenic hydrocarbons under normal conditions, the pressure is between 10 and 50 bars depending on the relative proportion of the ethylenic hydrocarbon and the alkali or alkaline-earth metal hydroxide.

The reaction time is 0.5 to 24 hours, for example.

The substances of the invention are liquid substances which generally contain 20% to 70% by weight of sulphur. They are clear and homogeneous even when the sulphur content is high. The colour varies depending on the nature of the starting hydrocarbon and the quantity of fixed sulphur. They may be very slightly or slightly coloured (for example with monoethylenic hydrocarbon such as isobutene) to highly coloured (for example with polyethylenic hydrocarbons).

With monoethylenic hydrocarbons, the sulphur-containing substances are characterised by a near absence of ethylenic carbon atoms.

The sulphur content of the substances of the invention confers them with antiwear and extreme pressure properties and they can advantageously be used as additives for lubricating oils and greases, in particular for oils for automobile gears and in industrial oils.

For these uses, the substances of the invention are generally incorporated into the lubricating compositions in concentrations of 0.05% to 20%, preferably 0.5% to 10% by weight.

Some of the sulphur-containing substances of the invention, in particular those deriving from the sulphurization of isobutene, can also be used as sulphurization agents, in particular for the preparation of catalysts for use in refining petroleum products.

The following examples illustrate the invention.

EXAMPLE 1

50 g (1.56 mole) of sulphur, 15 g (0.375 mole) of sodium hydroxide, 135 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 8 hours. The maximum pressure reached was 33 bars. After returning to room temperature, the medium was extracted with 150 ml of n-heptane. After washing with 10 weight % sodium hydroxide, then washing with water, the n-heptane was evaporated off under reduced pressure and 75 g of a clear liquid was obtained which had a sulphur content of 43.8% by weight.

EXAMPLE 2

75 g (2.34 mole) of sulphur, 15 g (0.375 mole) of sodium hydroxide, 135 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 8 hours. The maximum pressure reached was 30 bars. After returning to room temperature, the medium was extracted with 150 ml of n-heptane. After washing with 10 weight % sodium hydroxide, then washing with water, the n-heptane was evaporated off under reduced pressure and 103 g of a clear liquid was obtained which had a sulphur content of 55.4% by weight.

EXAMPLE 3

112.5 g (3.51 mole) of sulphur, 22.5 g (0.562 mole) of sodium hydroxide, 202 g of water and 72 g (1.285 mole) of isobutene were introduced into 1 liter reactor which could operate under pressure and which was provided with a stirrer, a system for introducing liquid or gaseous reactants, and a system for controlling the temperature and the pressure. The medium was heated at 130° C. for 10 hours. The maximum pressure reached was 32 bars. After returning to room temperature, the medium was extracted with 150 ml of n-heptane. After washing with 10 weight % sodium hydroxide, then washing with water, the n-heptane was evaporated off under reduced pressure and 154 g of a clear liquid was obtained which had a sulphur content of 57.4% by weight.

EXAMPLE 4

35.7 g (1.11 mole) of sulphur, 7.5 g (0.187 mole) of sodium hydroxide, 68 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 8 hours. The maximum pressure reached was 32 bars. After returning to room temperature, the medium was extracted with 150 ml of n-heptane. After washing with 10 weight % sodium hydroxide, then washing with water, the n-heptane was evaporated off under reduced pressure and 54 g of a clear liquid was obtained which had a sulphur content of 55.9% by weight.

EXAMPLE 5

225 g (7.03 mole) of sulphur, 45 g (1.125 mole) of sodium hydroxide, 405 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 10 hours. The maximum pressure reached was 32 bars. After returning to room temperature, the medium was extracted with 150 ml of toluene. After washing with 10 weight % sodium hydroxide, then washing with water, the toluene was evaporated off under reduced pressure and 213 g of a clear liquid was obtained which had a sulphur content of 64.5% by weight.

EXAMPLE 6

300 g (9.37 mole) of sulphur, 60 g (1.50 mole) of sodium hydroxide, 540 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 12 hours. The maximum pressure reached was 35 bars. After returning to room temperature, the medium was extracted with 150 ml of toluene. After washing with 10 weight % sodium hydroxide, then washing with water, the toluene was evaporated off under reduced pressure and 232 g of a clear liquid was obtained which had a sulphur content of 67.4% by weight.

EXAMPLE 7

75 g (2.34 mole) of sulphur, 7.5 g (0.187 mole) of sodium hydroxide, 135 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 8 hours. The maximum pressure reached was 31 bars. After returning to room temperature, the medium was extracted with 150 ml of toluene. After washing with 10 weight % sodium hydroxide, then washing with water, the toluene was evaporated off under reduced pressure and 86 g of a clear liquid was obtained which had a sulphur content of 63% by weight.

EXAMPLE 8

75 g (2.34 mole) of sulphur, 30 g (0.75 mole) of sodium hydroxide, 135 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 10 hours. The maximum pressure reached was 32 bars. After returning to room temperature, the medium was extracted with 150 ml of n-heptane. After washing with 10 weight % sodium hydroxide, then washing with water, the n-heptane was evaporated off under reduced pressure and 68 g of a clear liquid was obtained which had a sulphur content of 56.8% by weight.

EXAMPLE 9

112.5 g (3.52 mole) of sulphur, 0.2 g (0.005 mole) of sodium hydroxide, 400 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 145° C. for 12 hours. The maximum pressure reached was 36 bars. After returning to room temperature, the medium was extracted with 150 ml of n-heptane. After washing with 10 weight % sodium hydroxide, then washing with water, the n-heptane was evaporated off under reduced pressure and 100 g of a clear liquid was obtained which had a sulphur content of 61.5% by weight.

EXAMPLE 10

225 g (7.03 mole) of sulphur, 0.2 g (0.005 mole) of sodium hydroxide, 400 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 140° C. for 12 hours. The maximum pressure reached was 38 bars. After returning to room temperature, the medium was extracted with 150 ml of toluene. After washing with 10 weight % sodium hydroxide, then washing with water, the toluene was evaporated off under reduced pressure and 90 g of a clear liquid was obtained which had a sulphur content of 67.0% by weight.

EXAMPLE 11

35 g (1.09 mole) of sulphur, 15 g (0.375 mole) of sodium hydroxide, 135 g of water and 70 g (0.83 mole) of 2,3-dimethyl 1-butene were introduced into a 1 liter reactor which could operate under pressure and which was provided with a stirrer, a system for introducing liquid or gaseous reactants, and a system for controlling the temperature and the pressure. The medium was heated at 130° C. for 10 hours. The maximum pressure reached was 10 bars. After returning to room temperature, the medium was extracted with 150 ml of n-heptane. After washing with 10 weight % sodium hydroxide, then washing with water, the n-heptane was evaporated off under reduced pressure and 40 g of a clear liquid was obtained which had a sulphur content of 39.3% by weight.

EXAMPLE 12

39.5 g (1.23 mole) of sulphur, 15 g (0.375 mole) of sodium hydroxide, 135 g of water and 75 g (0.567 mole) of dicyclopentadiene were introduced into a 1 liter reactor which could operate under pressure and which was provided with a stirrer, a system for introducing liquid or gaseous reactants, and a system for controlling the temperature and the pressure. The medium was heated at 130° C. for 12 hours. The maximum pressure reached was 7 bars. After returning to room temperature, the medium was extracted with 150 ml of toluene. After washing with 10 weight % sodium hydroxide, then washing with water, the toluene was evaporated off under reduced pressure and 82 g of a clear liquid was obtained which had a sulphur content of 20.9% by weight.

EXAMPLE 13

50 g (1.56 mole) of sulphur, 15 g (0.375 mole) of sodium hydroxide, 135 g of water and 67 g (1.196 mole) of isobutene and 3.6 g (0.064 mole) of 1,3-butadiene were introduced into a 1 liter reactor which could operate under pressure and which was provided with a stirrer, a system for introducing liquid or gaseous reactants, and a system for controlling the temperature and the pressure. The medium was heated at 130° C. for 12 hours. The maximum pressure reached was 30 bars. After returning to room temperature, the medium was extracted with 150 ml of n-heptane. After washing with 10 weight % sodium hydroxide, then washing with water, the n-heptane was evaporated off under reduced pressure and 55 g of a clear liquid was obtained which had a sulphur content of 51.9% by weight.

EXAMPLE 14

76.9 g (2.40 mole) of sulphur, 15 g (0.375 mole) of sodium hydroxide, 135 g of water, 36.5 g (0.652 mole) of isobutene and 46.7 g (0.35 mole) of dicyclopentadiene were introduced into a 1 liter reactor which could operate under pressure and which was provided with a stirrer, a system for introducing liquid or gaseous reactants, and a system for controlling the temperature and the pressure. The medium was heated at 130° C. for 10 hours. The maximum pressure reached was 21 bars. After returning to room temperature, the medium was extracted with 150 ml of toluene. After washing with 10 weight % sodium hydroxide, then washing with water, the toluene was evaporated off under reduced pressure and 126 g of a clear liquid was obtained which had a sulphur content of 42.5% by weight.

EXAMPLE 15

112.5 g (3.51 mole) of sulphur, 0.2 g (0.0036 mole) of potassium hydroxide, 400 g of water and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 12 hours. The maximum pressure reached was 39 bars. After returning to room temperature, the medium was extracted with 150 ml of n-heptane. After washing with 10 weight % sodium hydroxide, then washing with water the n-heptane was evaporated off under reduced pressure and 130 g of a clear liquid was obtained which had a sulphur content of 64.5% by weight.

C13 NMR examination and elementary analysis of the substances prepared as described in Examples 1 to 11 and 15 indicated the absence of ethylenic carbon atoms and the absence of sodium in all the substances of Examples 1 to 15.

EXAMPLE 16

Examination of the Solubility of the Substances of the Invention

The solubilities of substances of the invention, prepared as described in Examples 1 to 11, were examined in a 130 Neutral Solvent mineral oil and in a synthetic hydrogenated polyalphaolefinic oil (PAO 6), at a concentration which kept the sulphur content to 2% by weight. The results are shown in Table I.

EXAMPLE 17

Charcterisation of Extreme Pressure Properties

The extreme pressure properties of the substances of the invention, prepared as described in Examples 1, 2, 3, 5, 6 and 7, were examined in a 130 Neutral Solvent mineral oil at a concentration which kept the sulphur content due to the additive to 2% by weight. Characterisation was carried out using a 4 ball machine according to standard ASTM D2783. The results are shown in Table II.

EXAMPLE 18

75 g (2.34 mole) of sulphur, 15 g (0.375 mole) of sodium hydroxide, 15 g of water, 150 ml of ethyleneglycol and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 9 hours. The maximum pressure reached was 28 bars. After returning to room temperature, the medium was extracted with 150 ml of n-heptane. After washing with 10 weight % sodium hydroxide, then washing with water, the n-heptane was evaporated off under reduced pressure and 93 g of a clear liquid was obtained which had a sulphur content of 48.4% by weight.

EXAMPLE 19

75 g (2.34 mole) of sulphur, 15 g (0.375 mole) of sodium hydroxide, 15 g of water, 150 ml of propyleneglycol and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 12 hours. The maximum pressure reached was 30 bars. After returning to room temperature, the medium was extracted with 150 ml of n-heptane. After washing with 10 weight % sodium hydroxide, then washing with water, the n-heptane was evaporated off under reduced pressure and 102 g of a clear liquid was obtained which had a sulphur content of 48.4% by weight.

EXAMPLE 20

150 g (4.68 mole) of sulphur, 30 g (0.75 mole) of sodium hydroxide, 150 ml of ethyleneglycol and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 10 hours. The maximum pressure reached was 31 bars. After returning to room temperature, the medium was extracted with 150 ml of n-heptane. After washing with 10 weight % sodium hydroxide, then washing with water, the n-heptane was evaporated off under reduced pressure and 164 g of a clear liquid was obtained which had a sulphur content of 57.2% by weight.

EXAMPLE 21

150 g (4.68 mole) of sulphur, 0.2 g (0.75 mole) of sodium hydroxide, 150 ml of ethyleneglycol and 72 g (1.285 mole) of isobutene were introduced into a 1 liter reactor which could operate under pressure and which was provided with a stirrer, a system for introducing liquid or gaseous reactants, and a system for controlling the temperature and the pressure. The medium was heated at 130° C. for 12 hours. The maximum pressure reached was 31 bars. After returning to room temperature, the medium was extracted with 150 ml of n-heptane. After washing with 10 weight % sodium hydroxide, then washing with water, the n-heptane was evaporated off under reduced pressure and 34 g of a clear liquid was obtained which had a sulphur content of 60.3% by weight.

EXAMPLE 22

75 g (2.34 mole) of sulphur, 15 g (0.375 mole) of sodium hydroxide, 150 ml of ethyleneglycol, 67.1 g (1.2 mole) of isobutene and 3.6 g (0.064 mole) of 1,3-butadiene were introduced into a 1 liter reactor which could operate under pressure and which was provided with a stirrer, a system for introducing liquid or gaseous reactants, and a system for controlling the temperature and the pressure. The medium was heated at 130° C. for 10 hours. The maximum pressure reached was 25 bars. After returning to room temperature, the medium was extracted with 150 ml of n-heptane. After washing with 10 weight % sodium hydroxide, then washing with water, the n-heptane was evaporated off under reduced pressure and 34 g of a clear liquid was obtained which had a sulphur content of 50.6% by weight.

C13 NMR examination and elementary analysis of the substances prepared as described in Examples 18 to 21 indicated the absence of ethylenic carbon atoms and the absence of sodium in all the substances prepared as described in Examples 18 to 22.

EXAMPLE 23

Examination of the Solubility of the Substances of the Invention

The solubilities of substances of the invention, prepared as described in Examples 18 to 22, were examined in a 130 Neutral Solvent mineral oil and in a synthetic hydrogenated polyalphaolefinic oil (PAO 6), at a concentration which kept the sulphur content to 2% by weight. The results are shown in Table III.

EXAMPLE 24

Characterisation of Extreme Pressure Properties

The extreme pressure properties of the substances of the invention, prepared as described in Examples 18 to 21, were examined in a 130 Neutral Solvent mineral oil at a concentration which kept the sulphur content due to the additive to 2% by weight. Characterisation was carried out using a 4 ball machine according to standard ASTM D2783. The results are shown in Table IV.

TABLE I

| PRODUCT FROM EXAMPLE NO | ADDITIVE/ OIL wt % | S/ OIL wt % | SOLUBILITY/ MINERAL OIL 130N | SOLUBILITY/ SYNTHETIC OIL PAO 6 |
| --- | --- | --- | --- | --- |
| 1 | 4.56 | 2 | yes | yes |
| 2 | 3.61 | " | yes | yes |
| 3 | 3.48 | " | yes | yes |
| 4 | 3.57 | " | yes | yes |
| 5 | 3.1 | " | yes | yes |
| 6 | 2.96 | " | yes | yes |
| 7 | 3.17 | " | yes | yes |
| 8 | 3.52 | " | yes | yes |
| 9 | 3.25 | " | yes | yes |
| 10 | 2.98 | " | yes | yes |
| 11 | 5.08 | " | yes | yes |

TABLE II

| PRODUCT FROM EXAMPLE NO | ADDITIVE/ OIL wt % | S/ OIL wt % | 4 BALL MACHINE TESTS | |
| --- | --- | --- | --- | --- |
| | | | Welding load (daN) | load/wear index (daN) |
| 1 | 4.56 | 2 | 380 | 71 |
| 2 | 3.61 | " | 430 | 80 |
| 3 | 3.48 | " | 410 | 79 |
| 5 | 3.1 | " | 400 | 77 |
| 6 | 2.96 | " | 390 | 72 |
| 7 | 3.17 | " | 440 | 84 |

TABLE III

| PRODUCT FROM EXAMPLE NO | ADDITVE/ OIL wt % | S/ OIL wt % | SOLUBILITY/ MINERAL OIL 130N | SOLUBILITY/ SYNTHETIC OIL PAO 6 |
| --- | --- | --- | --- | --- |
| 18 | 4.13 | 2 | yes | yes |
| 19 | 4.13 | " | yes | yes |
| 20 | 3.49 | " | yes | yes |
| 21 | 3.32 | " | yes | no |
| 22 | 3.95 | " | yes | yes |

TABLE IV

| PRODUCT FROM EXAMPLE NO | ADDITIVE/ OIL wt % | S/ OIL wt % | 4 BALL MACHINE TESTS | |
| --- | --- | --- | --- | --- |
| | | | Welding load (daN) | load/wear index (daN) |
| 18 | 4.13 | 2 | 410 | 80 |
| 19 | 4.13 | " | 400 | 74 |
| 20 | 3.49 | " | 390 | 72 |
| 21 | 3.32 | " | 420 | 81 |

We claim:

1. A process for the production of a sulphur-containing substance, comprising reacting a hydrocarbon consisting of at least one monoethylenic hydrocarbon containing 2 to 36 carbon atoms with a sulfur-containing material consisting of elemental sulphur in the presence of an at least one alkali or alkaline-earth metal hydroxide and at least one glycol or polyglycol with a molecular weight of up to about 200, an alkyl ether derivative thereof, and/or water.

2. A process according to claim 1, wherein the monoethylenic hydrocarbon is ethylene, propylene, 1-butene, a n-2-butene, isobutene, a pentene, a hexene, a dimer or trimer of isobutene, a trimer or tetramer of propylene, or a non-hydrogenated polyaphoaolefin with a molecular weight of up to about 500.

3. A process to claim 1, wherein said hydrocarbon is isobutene.

4. A process according to claim 1, wherein the reaction is conducted in the presence of water and sodium hydroxide, potassium hydroxide, lithium hydroxide, calcium hydroxide or barium hydroxide in an amount of $3 \times 10^{-3}$ to 1.2 moles per ethylenic unsaturation of the starting hydrocarbon.

5. A process according to claim 1, wherein the reaction is conducted in the presence of glycol, polyglycol or glycol monoether in a proportion of 10 to 150 g per ethylenic unsaturation in the monoethylenic hydrocarbon.

6. A process according to claim 1, wherein water is used in a proportion of 50 to 500 $cm^3$ per ethylenic unsaturation in the starting hydrocarbon.

7. A process according to claim 1, wherein the reaction is carried out at a temperature of 50° C. to 200° C. at a pressure of between atmospheric pressure up to 50 bars.

8. A process according to claim 1, wherein the reaction is conducted in the presence of a glycol, a polyglycol or an alkyl ether derivative of glycol or a polyglycol and at least one alkali metal which is sodium hydroxide, potassium hydroxide, lithium hydroxide, calcium hydroxide or barium hydroxide in a proportion of 0.004 to 1 mole per ethylenic unsaturation of the starting hydrocarbon.

9. A process according to claim 1, wherein the sulphurization is conducted to the extent of providing a final product with at least 60.3% by weight of sulphur.

10. A process according to claim 1, wherein in the proportion of elemental sulfur is up to 250 g per ethylenic unsaturation in the starting hydrocarbon.

11. A porcess according to claim 1, wherein the monoethylenic hydrocabo contains 2–9 or 11–36 carbon atoms.

* * * * *